United States Patent [19]

Guttag

[11] Patent Number: 5,657,777
[45] Date of Patent: Aug. 19, 1997

[54] GERMICIDAL MASCARA APPLICATOR BRUSH

[76] Inventor: Alvin Guttag, 415 Russell Ave. Apt. 108, Gaithersburg, Md. 20877-2845

[21] Appl. No.: 574,342

[22] Filed: Dec. 18, 1995

[51] Int. Cl.$^6$ ............................ A45D 40/26; A45B 11/00
[52] U.S. Cl. ........................ 132/218; 424/707; 132/317; 401/125; 401/129
[58] Field of Search ............................. 424/707; 132/218

[56] References Cited

U.S. PATENT DOCUMENTS 5,526,546  6/1996  Kamen ................................. 15/207.2

Primary Examiner—Jyothsna Venkat
Attorney, Agent, or Firm—Cushman Darby & Cushman IP Group of Pillsbury Madison & Sutro, LLP

[57] ABSTRACT

The present invention reveals a mascara applicator brush useful for preventing or eliminating contamination from use. The mascara applicator brush is made of bristles, where the bristles are (1) made from an oligodynamic metal, (2) coated with at least an oligodynamic metal or a germicide or (3) made from a polymer containing at least an oligodynamic metal or a germicide.

21 Claims, No Drawings

GERMICIDAL MASCARA APPLICATOR BRUSH

BACKGROUND OF THE INVENTION

1. Field of the Invention

The present invention relates to a mascara applicator brush useful for preventing or eliminating contamination from use. More specifically, the mascara applicator brush of the present invention is made of bristles, wherein the bristles are (1) made from an oligodynamic metal, (2) coated with at least an oligodynamic metal or a germicide or (3) made from a polymer containing at least an oligodynamic metal or a germicide.

2. Description of the Related Art

When an applicator (applicator brush) is used to apply mascara or a lotion to eyelashes or eyelids and then is placed back in a bottle (an applicator bottle or container), there is a danger that the applicator has become contaminated with microorganisms, e.g., bacteria or fungi from the skin or eyelashes which have contacted the applicator. It was recently suggested on television that the applicator and bottle should be thrown away after a few months apparently due to contamination of the applicator.

The various manufacturers of mascara such as Revlon, Maybelline and L'Oreal include germicides in their mascara formulations. For example, the L'Oreal Waterproof Lashout® product literature states that the product was made under U.S. Pat. No. 4,871,536 and that the formulation, including quaternium 18, bentonite, polyquaternium 10 and methyl paraben, is patent pending. However, the inclusion of germicidal components in the formulation is not sufficient to prevent microorganisms from contaminating the applicator brush.

Thus, the present inventor sought to eliminate the problem of contamination of the applicator brush from use.

SUMMARY OF THE INVENTION

The present invention discloses a mascara applicator brush comprised of bristles, wherein the bristles are (1) made from an oligodynamic metal, (2) coated with at least an oligodynamic metal or a germicide or (3) made from a polymer containing at least an oligodynamic metal or a germicide.

Representative examples of the oligodynamic metal include silver, gold and iron.

Representative examples of the germicide include cetyl pyridinium chloride, a mixture of trimethoprim and sulfamethoxazole, cefaperazone sodium, polymyxin B sulfate-neomycin sulfate, povidone-iodine, amphotericin B, bectomethasone dipropionate monohydrate, penicillin, oxytetracycline, streptomycin, erythromycin, bacitracin, tetracycline, gramicidin, tyrocidin, viomycin, aureomycin and neomycin.

The polymer used to make the bristles of the mascara applicator brush of the present invention can be either a hydrophobic or hydrophilic polymer. Furthermore, representative examples of the polymers include natural rubber, butadiene-styrene copolymer, butadiene-acrylonitrile copolymer, hydroxyethyl methacrylate-ethylene glycol dimethacrylate copolymer, polychloroprene and polyethylene.

In addition, the bristles of the mascara applicator brush can be coated with both an oligodynamic metal and a germicide. Likewise, the bristles of the mascara applicator brush can be made from a polymer containing both an oligodynamic metal and a germicide.

Finally, the mascara brush applicator of the present invention is used in combination with a mascara applicator bottle.

DETAILED DESCRIPTION OF THE INVENTION

The problem of contamination of the applicator by use was prevented or eliminated:

a) by making the bristles of an applicator brush from an oligodynamic metal, b) by coating the bristles with an oligodynamic metal or a germicide or c) by making the bristles from a polymer containing an oligodynamic metal or a germicide.

In regard to making the bristles of an applicator brush out of an oligodynamic metal, an oligodynamic metal is defined as a metal which inhibits the growth of microorganisms. Examples of oligodynamic metals include gold, silver and iron. Thus, by making the bristles of an applicator brush out of an oligodynamic metal, the problem of contamination of the applicator is eliminated.

In regard to coating the bristles with an oligodynamic metal or a germicide, the bristles of the applicator can be made of nylon, polyethylene terephthalate, rayon, polyethylene, hair, wool, cellulosic fibers or other fibers. The bristles can then be coated with a germicide, e.g., a bactericide and/or fungicide. The bristles can also be coated with an oligodynamic metal. The oligodynamic metal can be in a finely divided form or in the form of a film. Thus, by coating the bristles with an oligodynamic metal or a germicide, the problem of contamination of the applicator is eliminated.

In regard to making the bristles out of a polymer containing an oligodynamic metal or a germicide, the bristles can be made of a hydrophobic or hydrophilic polymer containing an oligodynamic metal or a germicide incorporated therein. Thus, by making the bristles out of a polymer containing an oligodynamic metal or a germicide, the problem of contamination of the applicator is eliminated.

The advantage of using a hydrophilic polymer containing a germicide for the bristles or for coating the bristles is that germicide can be continually leached to the surface to maintain germicidal (e.g., microbicidal, bactericidal and/or fungicidal) action. In addition, liquid from the mascara can go into the interior of the brush to insure that the germicidal action is maintained. The rate of leaching through the polymer can be controlled, e.g., in a copolymer, by varying the ratio of hydrophilic to hydrophobic components of the polymer. Generally, the higher the percentage of the hydrophobic component, the slower the rate of leaching.

Examples of typical suitable plastics and elastomers that can be used to make and/or coat the bristles of the mascara applicator brush are those set forth in U.S. patent application 08/294,400 (Guttag), filed Aug. 23, 1994, now pending, the entire disclosure of which is hereby incorporated by reference and relied upon.

Typical hydrophobic synthetic resin plastics include polymers such as those set forth in U.S. Pat. No. 4,952,426 (Guttag) in column 2, lines 42–62 and column 3, lines 14–22, the entire disclosure of which is hereby incorporated by reference and relied upon. Illustrative elastomers include natural rubber, butadiene-styrene copolymer, butadiene-acrylonitrile copolymer and polychloroprene.

Typical hydrophilic synthetic resins include those set forth in U.S. Pat. No. 3,633,546 (Guttag) in column 1, line 61 to column 3, line 32 and U.S. Pat. No. 3,767,790 (Guttag) in column 3, line 13 to column 4, line 62, the entire disclosure of which is hereby incorporated by reference and relied upon. The hydrophilic polymers permit the germicide to leach to the outside of the bristles and continually renew the germicidal action.

Illustrative germicides include those set forth in U.S. patent application 08/294,400 (Guttag), filed Aug. 23, 1994, now pending, the entire disclosure of which is hereby incorporated by reference and relied upon. Illustrative germicides include cetyl pyridinium chloride, Bactrin (a mixture of 160 mg trimethoprim and 800 mg of sulfamethoxazole), Cefobid (cefaperazone sodium), Neosporin (polymyxin B sulfate-neomycin sulfate), Betadine (povidone-iodine), Fungizone (Amphotericin B), Beconase (Bectomethasone dipropionate monohydrate), penicillin, oxytetracycline, streptomycin, erythromycin, bacitracin, tetracycline, gramicidin, tyrocidin, viomycin, aureomycin, neomycin.

The following non-limiting examples are used to illustrate the present invention. Unless otherwise indicated all parts and percentages are by weight.

EXAMPLES

1. Making Bristles Out of an Oligodynamic Metal

In a typical example, the bristles of an applicator are made entirely of silver. The applicator is then placed in the applicator bottle.

2. Coating Bristles With a Polymer Containing an Oligodynamic Metal

In this example, the bristles of an applicator are coated with molten polyethylene containing 10% by weight finely divided silver. The applicator is then placed in the applicator bottle.

3. Coating Bristles With a Polymer Containing a Germicide

In this example, the bristles of an applicator are coated with a hydrophilic copolymer of 100 parts of 2-hydroxyethyl methacrylate and 0.5 parts of ethylene glycol dimethacrylate saturated with cetyl pyridinium chloride. The coating can be adhered to the bristles with an adhesive, e.g., using a molten polymer such as polyethylene. The applicator is then placed in the applicator bottle.

4. Coating Bristles With a Polymer Containing an Oligodynamic Metal and a Germicide In this example, the bristles of an applicator are coated with a mixture of finely divided silver and 25% Bactrin based on the weight of the silver. Again, the coating can be adhered to the bristles with an adhesive, e.g., using a molten polymer such as polyethylene. The applicator is then placed in the applicator bottle.

5. Making Bristles Out of a Polymer Containing an Oligodynamic Metal

In this example, the bristles of an applicator are made of a copolymer of 100 parts of 2-hydroxyethyl methacrylate and 0.5 parts of ethylene glycol dimethacrylate containing 10% by weight finely divided silver. The applicator is then placed in the applicator bottle.

6. Making Bristles Out of a Polymer Containing a Germicide

In this example, the bristles of an applicator are made of the hydroxyethyl methacrylate-ethylene glycol dimethacrylate copolymer of Example 5 saturated with cetyl pyridinium chloride. The applicator is then placed in the applicator bottle.

7. Making Bristles Out of a Polymer Containing an Oligodynamic Metal and a Germicide In this example, the bristles of an applicator are made of the hydroxyethyl methacrylate-ethylene glycol dimethacrylate copolymer of Example 5 containing 10% by weight finely divided silver and saturated with cetyl pyridinium chloride. The applicator is then placed in the applicator bottle.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims.

The entire disclosure of all patents, patent applications, product literature and publications cited herein are hereby incorporated by reference and relied upon.

What is claimed is:

1. A mascara applicator brush comprised of bristles wherein said bristles are either:
   a) bristles made from an oligodynamic metal;
   b) bristles which are coated with at least one of an oligodynamic metal or germicide; or
   c) bristles made from a polymer containing at least one of an oligodynamic metal or a germicide.

2. The mascara applicator brush of claim 1, wherein there is present an oligodynamic metal and said oligodynamic metal is selected from the group consisting of silver, gold and iron.

3. The mascara applicator brush of claim 1, wherein the germicide is selected from the group consisting of cetyl pyridinium chloride, a mixture of trimethoprim and sulfamethoxazole, cefaperazone sodium, polymyxin B sulfate-neomycin sulfate, povidone-iodine, amphotericin B, bectomethasone dipropionate monohydrate, penicillin, oxytetracycline, streptomycin, erythromycin, bacitracin, tetracycline, gramicidin, tyrocidin, viomycin, aureomycin and neomycin.

4. The mascara applicator brush of claim 1, wherein the bristles are made from a polymer containing at least an oligodynamic metal or a germicide and the polymer is a hydrophobic or hydrophilic polymer.

5. The mascara applicator brush of claim 4, wherein the polymer is selected from the group consisting of natural rubber, butadiene-styrene copolymer, butadiene-acrylonitrile copolymer, hydroxyethyl methacrylate-ethylene glycol dimethacrylate copolymer, polychloroprene and polyethylene.

6. The mascara applicator brush of claim 1, wherein said bristles are b).

7. The mascara applicator brush of claim 1, wherein said bristles are c).

8. A mascara applicator bottle containing the mascara applicator brush of claim 1.

9. The mascara applicator brush of claim 1, wherein the bristles are coated with an oligodynamic metal.

10. The mascara applicator brush of claim 1, wherein the bristles are made from a polymer containing an oligodynamic metal.

11. The mascara applicator brush of claim 1, wherein the bristles are made from a polymer containing a germicide.

12. The mascara applicator brush of claim 1, wherein the bristles are coated with at least an oligodynamic metal or a germicide and the oligodynamic metal or germicide is contained in a hydrophobic polymer or a hydrophilic polymer.

13. The mascara applicator brush of claim 12, wherein the polymer is a hydrophilic polymer.

14. The mascara applicator brush of claim 12, wherein the polymer is a hydrophobic polymer.

15. The mascara applicator bottle of claim 8, wherein the applicator brush bristles are made of a hydrophobic polymer or hydrophilic polymer containing at least an oligodynamic metal or a germicide.

16. The mascara applicator bottle of claim 8, wherein the applicator brush bristles are coated with a hydrophobic polymer or hydrophilic polymer, said polymer containing at least an oligodynamic metal or a germicide.

17. A mascara applicator brush according to claim 1, wherein an oligodynamic metal is present and said oligodynamic metal is gold.

18. A mascara applicator brush according to claim 1, wherein an oligodynamic metal is present and said oligodynamic metal is silver.

19. A mascara applicator brush according to claim 1, wherein the bristles are either b) or c) and the bristles are either b) bristles coated with both an oligodynamic metal and a germicide, or c) bristles made from a polymer containing both an oligodynamic metal and a germicide.

20. A mascara applicator brush according to claim 1, wherein the bristles are b) in which the bristles are formed from nylon, polyethylene terephthalate, rayon, polyethylene, hair, wool or cellulosic fibers.

21. A mascara applicator brush according to claim 20, wherein the bristles are made from nylon.

* * * * *